(12) United States Patent
Wang et al.

(10) Patent No.: US 8,653,309 B2
(45) Date of Patent: *Feb. 18, 2014

(54) PROCESS FOR PRODUCING TRANS-1233ZD

(75) Inventors: Haiyou Wang, Amherst, NY (US);
Hsueh Sung Tung, Getzville, NY (US)

(73) Assignee: Honeywell International Inc.,
Morristown, NJ (US)

( * ) Notice: Subject to any disclaimer, the term of this patent is extended or adjusted under 35 U.S.C. 154(b) by 13 days.

This patent is subject to a terminal disclaimer.

(21) Appl. No.: 13/090,477

(22) Filed: Apr. 20, 2011

(65) Prior Publication Data

US 2012/0271069 A1 Oct. 25, 2012

(51) Int. Cl.
| | |
|---|---|
| C07C 17/00 | (2006.01) |
| C07C 21/18 | (2006.01) |
| C07C 23/00 | (2006.01) |
| C07C 25/00 | (2006.01) |
| C07C 21/00 | (2006.01) |
| C07C 17/25 | (2006.01) |
| C07C 19/08 | (2006.01) |

(52) U.S. Cl.
USPC ............ 570/151; 570/153; 570/155; 570/156

(58) Field of Classification Search
None
See application file for complete search history.

(56) References Cited

U.S. PATENT DOCUMENTS

| | | | |
|---|---|---|---|
| 2,898,383 | A | 8/1959 | Eisenlohr et al. |
| 3,857,882 | A | 12/1974 | Auer et al. |
| 4,145,492 | A | 3/1979 | Gardner |
| 5,710,352 | A | 1/1998 | Tung |
| 6,844,475 | B1 | 1/2005 | Tung et al. |
| 7,829,747 | B2 | 11/2010 | Wang et al. |
| 8,217,208 | B2 * | 7/2012 | Hulse et al. ................ 570/236 |
| 2007/0129579 | A1 | 6/2007 | Wang et al. |
| 2009/0043137 | A1 | 2/2009 | Wang et al. |
| 2009/0149680 | A1 | 6/2009 | Wang et al. |
| 2010/0152504 | A1 * | 6/2010 | Hulse et al. ................ 570/151 |
| 2010/0210882 | A1 | 8/2010 | Sharratt et al. |
| 2011/0005914 | A1 | 1/2011 | Tripper et al. |

FOREIGN PATENT DOCUMENTS

| | | | |
|---|---|---|---|
| CN | 1876238 A | 12/2006 | |
| CN | 101168494 * | 4/2008 | ............. C07C 21/18 |
| CN | 101168494 A | 4/2008 | |
| EP | 1916231 A2 | 4/2008 | |
| GB | 748130 | 4/1956 | |
| GB | 807501 | 1/1959 | |
| JP | 2008110980 A | 5/2008 | |
| KR | 20090112593 A | 4/2009 | |
| WO | 2010029893 A1 | 3/2010 | |
| WO | 2010059496 A1 | 5/2010 | |

OTHER PUBLICATIONS

CN-101168484 Machine Translation, 2008, p. 1-6.*
International Search Report and Written Opinion, issued Oct. 23, 2012, in corresponding International Patent Application No. PCT/US2012/032830.

* cited by examiner

*Primary Examiner* — Clinton Brooks
(74) *Attorney, Agent, or Firm* — Bruce O. Bradford

(57) ABSTRACT

Trans-1233zd, the trans-isomer of 1-chloro-3,3,3-trifluoropropene (HCFO-1233zd) can be used as blowing agents, solvents, cleaning agents, as well as monomers of macromolecule compounds, and can be prepared through the dehydrochlorination of 1,1,1-trifluoro-3,3-dichloropropane (HCFC-243fa) with the help of a catalyst. The present invention is directed to an integrated process is proposed to produce trans-1233zd from 243fa, which is consisted of the following four major unit operations: (1) Catalytic dehydrochlorination of 243fa into trans/cis-1233zd, (2) HCl recovery, (3) Catalytic isomerization of cis-1233zd into trans-1233zzd, and (4) Isolation of trans-1233zd.

12 Claims, No Drawings

PROCESS FOR PRODUCING TRANS-1233ZD

BACKGROUND OF THE INVENTION

Trans-1233zd, the trans-isomer of 1-chloro-3,3,3-trifluoropropene (HCFO-1233zd, or 1233zd), can be used as a blowing agent, solvent, cleaning agent, as well as a monomer for macromolecule compounds. Trans-1233zd can be prepared through the dehydrochlorination of 1,1,1-trifluoro-3,3-dichloropropane (HCFC-243fa, or 243fa) with the use of a catalyst. However, together with the desired trans-1233zd product, a cis-isomer is also generated as a by-product, which reduces the single pass yield of trans-1234zd. Therefore, there is a need for means by which cis-1233zd can be converted into trans-1233zd.

The following patents and patent applications are related to the subject matter of this invention. These documents are hereby incorporated herein by reference.

U.S. Pat. No. 5,710,352, entitled vapor phase process for making 1,1,3,3,3-pentafluoropropane and 1-chloro-3,3,3-trifluoropropene.

U.S. Pat. No. 6,844,475, entitled low temperature production of 1-chloro-3,3,3-trifluoropropene (1233zd).

U.S. Patent Publication No. 20100152504, entitled isomerization of 1-chloro-3,3,3-trifluoropropene.

SUMMARY OF THE INVENTION

In the present invention, an integrated process is disclosed for the production of trans-1233zd from 243fa, which comprises the following four major unit operations:
(1) Catalytic dehydrochlorination of 243fa to generate a mixture of trans and cis-1233zd,
(2) HCl recovery,
(3) Catalytic isomerization of cis-1233zd into trans-1233zd, and
(4) Isolation of the desired product, trans-1233zd.

To the inventors knowledge, no prior art teaches the production of 1233zd through the dehydrochlorination of 243fa. In addition, it is believed that a trans-1233zd manufacture process integrated with a cis-1233zd isomerization reactor has never before been reported in the prior art.

One embodiment of the invention thus provides a continuous, integrated manufacturing process for the production of trans-1-chloro-3,3,3-trifluoropropene which comprises:
(a) dehydrochlorinating 1,1,1-trifluoro-3,3-dichloropropane (243fa) in a reactor to thereby produce a product stream comprising cis-1-chloro-3,3,3-trifluoropropene, trans-1-chloro-3,3,3-trifluoropropene and hydrogen chloride;
(b) optionally recovering the hydrogen chloride from the product stream of step (a);
(c) isomerizing at least a portion of the cis-1-chloro-3,3,3-trifluoropropene into trans-1-chloro-3,3,3-trifluoropropene; and
(d) separating and purifying trans-1-chloro-3,3,3-trifluoropropene product.

In certain embodiments, the dehydrochlorination of 243fa is conducted in the vapor phase with a catalyst. Preferred catalysts are selected from the group consisting of halogenated metal oxide, metal halides, and supported metal catalysts. In certain embodiments, the dehydrochlorination of 243fa is conducted over fluorinated chromia catalyst.

In certain embodiments, the vapor phase reaction is conducted in a fixed-bed reactor. In certain embodiments, the 243fa is pre-vaporized prior to entering the reactor. In certain embodiments, the 243fa is vaporized inside the reactor.

In certain embodiments, the dehydrochlorination of 243fa is conducted with a caustic solution, which is essentially a liquid (whether a solution, dispersion, emulsion, or suspension and the like). In certain embodiments, the caustic solution is an aqueous solution of a base selected from the group consisting of KOH, NaOH, $Ca(OH)_2$ and CaO. In certain embodiments, the strength of the caustic solution is from about 2 wt. % to about 100 wt. %. In certain embodiments, the strength of the caustic solution is from about 5 wt. % to about 90 wt. %. In certain embodiments, the strength of the caustic solution is from about 10 wt. % to about 80 wt. %.

In certain embodiments, the cis-1233zd isomerization is conducted in the vapor phase with a catalyst. Preferably, the catalyst is selected from the group consisting of halogenated metal oxide, metal halides, and supported metal catalysts. In certain embodiments, the vapor phase isomerization reaction is conducted in a fixed-bed reactor.

Another embodiment of the invention provides a process for the production of trans-1-chloro-3,3,3-trifluoropropene comprising the steps of:
(a) dehydrochlorinating 1,1,1-trifluoro-3,3-dichloropropane (243fa) in a vapor phase reactor to thereby produce a product stream comprising cis-1-chloro-3,3,3-trifluoropropene, trans-1-chloro-3,3,3-trifluoropropene and hydrogen chloride;
(b) optionally recovering hydrogen chloride from the product stream of step (a);
(c) separating and purifying trans-1-chloro-3,3,3-trifluoropropene product; and
(d) sending the separated mixture of cis-1-chloro-3,3,3-trifluoropropene and 1,1,1-trifluoro-3,3-dichloropropane back to the vapor phase reactor of step (a) for recycle, wherein the 243fa is dehydrochlorinated into a mixture of trans- and cis-1233zd, and in addition, the cis-1233zd is isomerized into trans-1233zd.

DETAILED DESCRIPTION OF THE INVENTION

As described above, one embodiment of the invention provides a continuous, integrated manufacturing process for the production of trans-1-chloro-3,3,3-trifluoropropene which comprises:
(a) dehydrochlorinating 1,1,1-trifluoro-3,3-dichloropropane (243fa) in a reactor to thereby produce a product stream comprising cis-1-chloro-3,3,3-trifluoropropene, trans-1-chloro-3,3,3-trifluoropropene and hydrogen chloride;
(b) optionally recovering hydrogen chloride from the product stream of step (a);
(c) isomerizing at least a portion of the cis-1-chloro-3,3,3-trifluoropropene into trans-1-chloro-3,3,3-trifluoropropene; and
(d) separating and purifying trans-1-chloro-3,3,3-trifluoropropene product.

In a more preferred embodiment, the process for the production of trans-1-chloro-3,3,3-trifluoropropene comprises:
(a) dehydrochlorinating 1,1,1-trifluoro-3,3-dichloropropane (243fa) in a vapor phase reactor to thereby produce a product stream comprising cis-1-chloro-3,3,3-trifluoropropene, trans-1-chloro-3,3,3-trifluoropropene and hydrogen chloride;
(b) optionally recovering hydrogen chloride from the product stream of step (a);
(c) separating and purifying trans-1-chloro-3,3,3-trifluoropropene product; and
(d) sending the separated mixture of cis-1-chloro-3,3,3-trifluoropropene and 1,1,1-trifluoro-3,3-dichloropropane back to the vapor phase reactor of step (a) for recycle, in which not only 243fa is dehydrochlorinated into trans/cis-1233zd but also cis-1233zd is isomerized into trans-1233zd.

243fa Dehydrochlorination

The first step of the process involves the catalytic conversion of 243fa by dehydrochlorinating 243fa to produce a product stream comprising a combination of cis-1-chloro-3,3,3-trifluoropropene, trans-1-chloro-3,3,3-trifluoropropene and hydrogen chloride. Preferably dehydrochlorination of 243fa is done in a vapor phase, and more preferably in a fixed-bed reactor in the vapor phase.

The dehydrochlorination reaction may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel or vessels lined with fluoropolymers. These may be single pipe or multiple tubes packed with a dehydrochlorinating catalyst which may be one or more of halogenated metal oxides in bulk form or supported, metal halides in bulk form or supported, and carbon supported transition metals. Suitable catalysts non-exclusively include halogenated metal oxides (e.g., fluorinated $Cr_2O_3$, fluorinated $Al_2O_3$), metal halides (e.g., $CrF_3$, $AlF_3$, $AlCl_3$, $FeCl_3$) and carbon supported transition metals (zero oxidation state) such as Fe/C, Co/C, Ni/C, and Pd/C. The 243fa is introduced into the reactor either in pure form, impure form, or together with an optional inert gas diluent such as nitrogen, argon, or the like.

In a preferred embodiment of the invention, the 243fa is pre-vaporized or preheated prior to entering the reactor. Alternatively, the 243fa is vaporized inside the reactor. Useful reaction temperatures may range from about 200° C. to about 600° C. Preferred temperatures may range from about 250° C. to about 450° C., and more preferred temperatures may range from about 300° C. to about 350° C. The reaction may be conducted at atmospheric pressure, super-atmospheric pressure or under vacuum. The vacuum pressure can be from about 5 Ton to about 760 Ton. Contact time of the 243fa with the catalyst may range from about 0.5 seconds to about 120 seconds, however, longer or shorter times can be used.

In the preferred embodiment, the process flow is in either the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 200° C. to about 500° C., preferably from about 300° C. to about 400° C., for from about 0.5 hour to about 3 days. This is followed by $H_2$ treatment at temperatures of from about 100° C. to about 400° C., preferably from about 200° C. to about 300° C. for supported transition metal catalysts.

In an alternative embodiment of the invention, dehydrochlorination of 243fa can also be accomplished by reacting it with a strong caustic solution that includes, but is not limited to KOH, NaOH, $Ca(OH)_2$ and CaO, at an elevated temperature. The caustic solution is essentially a liquid (whether a solution, dispersion, emulsion, or suspension and the like). In certain embodiments, the caustic strength of the caustic solution is from about 2 wt. % to about 100 wt. %, more preferably from about 5 wt. % to about 90 wt. % and most preferably from about 10 wt. % to about 80 wt. %. The reaction may be conducted at a temperature of from about 20° C. to about 100° C., more preferably from about 40° C. to about 90° C. and most preferably from about 50° C. to about 70° C. As above, the reaction may be conducted at atmospheric pressure, super-atmospheric pressure or under vacuum. The vacuum pressure can be from about 5 Torr to about 760 Torr. In addition, a solvent may optionally be used to help dissolve the organic compounds in the caustic solution. This optional step may be conducted using solvents that are well known in the art for said purpose.

HCl Recovery

Optionally but preferably, hydrogen chloride is then recovered from the product stream of the dehydrochlorination reaction. The HCl in the crude intermediate stream is recovered using an HCl column. High purity HCl is isolated from the top of the column and absorbed in de-ionized water as concentrated HCl.

Alternatively, HCl can be recovered or removed from the product stream by using water or caustic scrubbers. When water extractor is used, HCl aqueous solution of various concentrations is formed. When caustic scrubber is used, HCl is neutralized as a chloride salt in aqueous solution.

HCFO-cis-1233zd Isomerization

At least a portion of the cis-1-chloro-3,3,3-trifluoropropene in the product stream is isomerized into trans-1-chloro-3,3,3-trifluoropropene. A stream of cis-1-chloro-3,3,3-trifluoropropene or its mixture with trans-1-chloro-3,3,3-trifluoropropene and/or 1,1,1-trifluoro-3,3-dichloropropane is fed into an isomerization reactor which contains a suitable isomerization catalyst to convert most of the cis-1233zd into trans-1233zd.

The isomerization reaction may be conducted in any suitable reaction vessel or reactor, but it should preferably be constructed from materials which are resistant to corrosion such as nickel and its alloys, including Hastelloy, Inconel, Incoloy, and Monel or vessels lined with fluoropolymers. These may be single pipe or multiple tubes packed with an isomerization catalyst which may be a halogenated metal oxide, a metal halide, or a carbon supported transition metal. Suitable catalysts non-exclusively include fluorinated chromia, chromium fluoride, fluorinated alumina, aluminum fluoride, alumina chloride, ferric chloride, and carbon supported iron, cobalt, nickel, or palladium.

Useful isomerization reaction temperatures range from about 25° C. to about 450° C. Preferred temperatures range from about 50° C. to about 350° C., and more preferred temperatures range from about 100° C. to about 250° C. The reaction may be conducted at atmospheric pressure, super-atmospheric pressure or under vacuum. The vacuum pressure can be from about 5 Torr to about 760 Torr. Contact time of the cis-1,3,3,3-tetrafluoropropene with the catalyst may range from about 0.5 seconds to about 120 seconds, however, longer or shorter times can be used.

HCFO-trans-1233zd Separation and Purification

Trans-1-chloro-3,3,3-trifluoropropene may be recovered from the reaction product mixture comprised of unconverted starting materials and by-products, including cis-1-chloro-3,3,3-trifluoropropene by any means known in the art, such as by extraction and preferably distillation. The distillation may be preferably conducted in a standard distillation column at atmospheric pressure, super-atmospheric pressure or a vacuum. Preferably the pressure is less than about 300 psig, more preferably less than about 150 psig and most preferably less than 100 psig. The pressure of the distillation column inherently determines the distillation operating temperature. Trans-1-chloro-3,3,3-trifluoropropene has a boiling point of about 19° C.; cis-1-chloro-3,3,3-trifluoropropene has a boiling point of about 38° C.; 243fa has a boiling point of from 71° C. to 74° C. Trans-1-chloro-3,3,3-trifluoropropene may be recovered as distillate by operating the distillation column at from about 30° C. to about 100° C. Single or multiple distillation columns may be used. The distillate portion includes substantially all the trans-1-chloro-3,3,3-trifluoropropene.

The overhead stream may then be further distillated to meet desired product specifications. The bottom stream of the distillation includes cis-1-chloro-3,3,3-trifluoropropene, 243fa, and any other impurities. The bottom stream may then be further distilled in another distillation column. The mixture of cis-1233zd and 243fa, recovered as a distillate, is then recycled back to the 243fa dehydrochlorination reactor in a preferred embodiment, where not only 243fa is dehydrochlorinated into a mixture of trans- and cis-1233zd, but in addition, the cis-1233zd is isomerized into trans-1233zd.

The following examples are served to demonstrate that the selected catalysts are, indeed, active for the dehydrochlorination of 243fa to form a mixture of cis- and trans-1233zd and for the isomerization of cis-1233zd to trans-1233zd.

EXAMPLE 1

Catalytic Dehydrochlorination of 243fa

Three different kinds of catalysts, namely, fluorinated metal oxide, metal halides, and supported metal, are used for 243fa dehydrochlorination in Example 1. In each case, 20 cc of catalyst is used. A 99.9% 243fa feed is flowed over catalyst at a rate of 12 g/h. As shown in Table 1, all the catalysts listed in Table 1 exhibit a high activity (>70% 243fa conversion) and a high selectivity to cis/trans-1233zd (>95%) during 243fa dehydrochlorination.

TABLE 1

243fa dehydrochlorination over various catalysts

| Catalyst | Temp., °C. | 243fa conv., % | Selectivity, % | | |
|---|---|---|---|---|---|
| | | | trans-1233zd | cis-1233zd | others |
| Fluorinated $Cr_2O_3$ | 250 | 91.0 | 90.6 | 8.5 | 0.9 |
| $AlF_3$ | 300 | 90.0 | 88.1 | 10.8 | 1.1 |
| 10 wt % $FeCl_3$/Carbon | 325 | 85.0 | 85.2 | 13.3 | 1.5 |
| 0.5 wt % Fe/AC | 425 | 75.0 | 79.2 | 18.6 | 2.2 |

Reaction conditions: 20 cc catalyst, 12 g/h 243fa, 1 atm

EXAMPLE 2

Isomerization of cis-1233zd over Selected Catalysts

Three different kinds of catalysts, namely, fluorinated metal oxide, metal halides, and supported metal, are used for cis-1233zd isomerization in Example 2. In each case, 20 cc of catalyst is used. A mixture of 88.0% cis-1233zd and 11.0% 243fa is flowed over catalyst at a rate of 12 g/h. For a specified catalyst, a suitable reaction temperature is carefully chosen such that almost no dehydrochlorination reaction occurs to the 243fa included in the feed.

As shown in Table 2, all the catalysts listed in Table 2 provide a cis-1233zd conversion above 40% and a trans-1233zd selectivity above 95% during cis-1233zd isomerization.

TABLE 2

Isomerization of cis-1233zd over Various Catalysts

| Catalyst | Reaction temp. (° C.) | Conversion, % cis-1233zd | Selectivity, % trans-1233zd |
|---|---|---|---|
| Fluorinated $Cr_2O_3$ | 100 | 68.0 | 99.9 |
| $AlF_3$ | 125 | 62.0 | 99.9 |
| 10 wt % $FeCl_3$/Carbon | 150 | 58.0 | 99.9 |
| 0.5 wt % Co/AC | 200 | 47.5 | 99.8 |

Reaction conditions: 20 cc catalyst, 12 g/h 88.0% cis-1233zd/11.0% 243fa, 1 atm

EXAMPLE 3

Combined 243fa Dehydrochlorination and cis-1233zd Isomerization over Fluorinated Chromia Catalyst The combined 243fa dehydrochlorination and cis-1233zd isomerization is conducted over fluorinated chromia catalyst in Example 3. 20 cc of catalyst is used. A mixture of 10.0% cis-1233zd/89.0% 243fa is flowed over catalyst at a rate of 12 g/h. Reaction temperature is carefully chosen such that both the 243fa dehydrofluorination and the cis-1233zd isomerization can take place.

As shown in Table 3, at a reaction temperature of 225° C., trans-1233zd is detected as the major component (>70%) in product stream and the percentages of both 243fa and cis-1233zd are lower in product stream than in feed stream. As a result, a high molar ratio of trans-1233zd to its cis-isomer (about 12) is realized. This example demonstrates that under optimal operation temperature the 243fa dehydrochlorination and the cis-1233zd isomerization can take place simultaneously in the same reactor.

TABLE 3

Combined 243fa Dehydrochlorination and cis-1233zd Isomerization over Fluorinated $Cr_2O_3$ Catalyst

| Component | Mol % in stream | |
|---|---|---|
| | before reaction | after reaction |
| 243fa | 89.0 | 17.8 |
| Trans-1233zd | 0.0 | 74.8 |
| cis-1233zd | 10.0 | 6.2 |
| Others | 1.0 | 1.2 |

Reaction conditions: 20 cc catalyst, 225° C., 1 atm, 12 g/h 10.0% cis-1233zd/89.0% 243fa While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A continuous, integrated manufacturing process for the production of trans-1-chloro-3,3,3-trifluoropropene which comprises:
   (a) dehydrochlorinating 1,1,1-trifluoro-3,3-dichloropropane (243 fa) to thereby produce a product stream comprising cis-1-chloro-3,3,3-trifluoropropene, trans-1-chloro-3,3,3-trifluoropropene and hydrogen chloride;

(b) optionally recovering the hydrogen chloride from the product stream of step (a);

(c) isomerizing at least a portion of the cis-1-chloro-3,3,3-trifluoropropene into trans-1-chloro-3,3,3-trifluoropropene; and (d) separating and purifying trans-1-chloro-3,3,3-trifluoropropene product wherein the dehydrochlorination of 243fa is conducted in the vapor phase with a catalyst selected from the group consisting of halogenated metal oxide, metal halides, and supported metal catalysts.

2. The process of claim 1, wherein the vapor phase reaction is conducted in a fixed-bed reactor.

3. The process of claim 2, wherein the 243fa is pre-vaporized prior to entering the reactor.

4. The process of claim 2, wherein the 243fa is vaporized inside the reactor.

5. The process of claim 1, wherein the dehydrochlorination of 243fa is conducted over fluorinated chromia catalyst.

6. The process of claim 1, wherein the cis-1233zd isomerization is conducted in the vapor phase with a catalyst selected from the group consisting of halogenated metal oxide, metal halides, and supported metal catalysts.

7. The process of claim 6, wherein the vapor phase isomerization reaction is conducted in a fixed-bed reactor.

8. The process of claim 6, wherein the isomerization of cis-1233zd is conducted over fluorinated chromia catalyst.

9. A process for the production of trans-1-chloro-3,3,3-trifluoropropene comprising the steps of:

(a) dehydrochlorinating 1,1,1-trifluoro-3,3-dichloropropane (243fa) in a vapor phase reactor to thereby produce a product stream comprising cis-1-chloro-3,3,3-trifluoropropene, trans-1-chloro-3,3,3-trifluoropropene and hydrogen chloride;

(b) optionally recovering hydrogen chloride from the product stream of step (a);

(c) separating and purifying trans-1-chloro-3,3,3-trifluoropropene product; and (d) sending the separated mixture of cis-1-chloro-3,3,3-trifluoropropene and 1,1,1-trifluoro-3,3-dichloropropane back to the vapor phase reactor of step (a) for recycle, wherein the 243fa is dehydrochlorinated into a mixture of trans- and cis-1233zd, and in addition, the cis-1233zd is isomerized into trans-1233zd.

10. The process of claim 9, wherein the cis-1233zd isomerization is conducted in the vapor phase with a catalyst selected from the group consisting of halogenated metal oxide, metal halides, and supported metal catalysts.

11. The process of claim 10, wherein the vapor phase isomerization reaction is conducted in a fixed-bed reactor.

12. The process of claim 10, wherein the isomerization of cis-1233zd is conducted over fluorinated chromia catalyst.

* * * * *